(12) United States Patent
Lilenthal

(10) Patent No.: US 9,861,530 B2
(45) Date of Patent: Jan. 9, 2018

(54) PROTECTIVE HEADGEAR AND OPTICAL-FILTER CARTRIDGE REMOVABLY MOUNTABLE THERETO

(71) Applicant: 3M INNOVATIVE PROPERTIES COMPANY, St. Paul, MN (US)

(72) Inventor: Niklas Lilenthal, Leksand (SE)

(73) Assignee: 3M Innovative Properties Company, St. Paul, MN (US)

( * ) Notice: Subject to any disclaimer, the term of this patent is extended or adjusted under 35 U.S.C. 154(b) by 182 days.

(21) Appl. No.: 14/925,620

(22) Filed: Oct. 28, 2015

(65) Prior Publication Data

US 2016/0051409 A1 Feb. 25, 2016

Related U.S. Application Data

(62) Division of application No. 13/761,433, filed on Feb. 7, 2013, now abandoned.

(51) Int. Cl.
*A61F 9/02* (2006.01)
*A61F 9/06* (2006.01)

(52) U.S. Cl.
CPC ............... *A61F 9/022* (2013.01); *A61F 9/06* (2013.01); *A61F 9/065* (2013.01); *A61F 2220/0033* (2013.01)

(58) Field of Classification Search
CPC .. A61F 9/022; A61F 9/06; A61F 9/065; A61F 2220/0033; A61F 9/061; A61F 9/062; A61F 9/064
USPC ................................................................ 2/12
See application file for complete search history.

(56) References Cited

U.S. PATENT DOCUMENTS

| | | | |
|---|---|---|---|
| 2,152,383 A | 3/1939 | Leader | |
| 2,270,028 A | 1/1942 | Anderson | |
| 2,411,224 A | 11/1946 | O'Reilly | |
| 2,907,041 A | 10/1959 | Finn | |
| 3,004,535 A | 10/1961 | Nielson | |
| 3,012,248 A | 12/1961 | Kleinman | |
| 3,056,140 A | 10/1962 | Lindblom | |
| 3,095,575 A | 7/1963 | Radov | |
| 3,411,158 A | 11/1968 | Benner | |
| 3,444,561 A | 5/1969 | Boyer | |
| 3,577,563 A | 5/1971 | Raschke | |
| 3,768,099 A * | 10/1973 | Manz | A61F 9/061 2/8.3 |
| 4,185,328 A | 1/1980 | Graveno | |
| 4,738,361 A | 4/1988 | Ackeret | |
| 4,774,723 A | 10/1988 | Ruck | |
| 4,875,235 A * | 10/1989 | Kuhlman | A61F 9/061 2/8.3 |

(Continued)

FOREIGN PATENT DOCUMENTS

| | | |
|---|---|---|
| CN | 101332139 A | 12/2008 |
| DE | 3626062 C2 | 2/1988 |

(Continued)

OTHER PUBLICATIONS

Extended European Search Report, EP14749141.9, dated Aug. 16, 2012.

*Primary Examiner* — Alissa L Hoey
(74) *Attorney, Agent, or Firm* — Kenneth B. Wood

(57) ABSTRACT

Protective headgear and an optical filter cartridge that is removably mountable thereto, and methods of removably inserting such a cartridge and removing such a cartridge.

13 Claims, 7 Drawing Sheets

(56) References Cited

U.S. PATENT DOCUMENTS

| | | |
|---|---|---|
| 5,062,156 A | 11/1991 | Siegal |
| 5,096,255 A | 3/1992 | Leischner |
| 5,224,219 A * | 7/1993 | Edwards ................ A61F 9/061 2/8.3 |
| 5,237,352 A | 8/1993 | Grosser |
| 5,302,815 A | 4/1994 | Eggenschwiler |
| 5,533,206 A * | 7/1996 | Petrie ..................... A61F 9/064 2/8.5 |
| 5,749,096 A | 5/1998 | Fergason |
| 6,067,129 A | 5/2000 | Fergason |
| 6,151,711 A | 11/2000 | Edwards |
| 6,185,739 B1 | 2/2001 | Verkic |
| 6,401,244 B1 | 6/2002 | Kramer |
| 6,557,174 B2 | 5/2003 | Martin |
| 6,923,537 B2 | 8/2005 | Hartley |
| 6,961,959 B2 | 11/2005 | Wang-Lee |
| 6,973,672 B2 | 12/2005 | Huh |
| 7,008,056 B2 | 3/2006 | Hartley |
| 7,161,116 B2 | 1/2007 | Steinemann |
| 7,284,281 B2 | 10/2007 | Huh |
| 7,308,719 B2 | 12/2007 | Huh |
| 7,537,399 B2 | 5/2009 | Mayumi |
| 7,823,224 B2 | 11/2010 | Fullerton |
| 7,933,122 B2 | 4/2011 | Richardson |
| 7,962,967 B2 | 6/2011 | Becker |
| 8,381,312 B2 | 2/2013 | Seo |
| 8,826,464 B2 | 9/2014 | Wu |
| 2004/0179149 A1 | 9/2004 | Wang-Lee |
| 2005/0273900 A1 | 12/2005 | DeYoung |
| 2008/0060102 A1 | 3/2008 | Matthews |
| 2008/0068521 A1 | 3/2008 | Cottier |
| 2009/0231423 A1 | 9/2009 | Becker |
| 2010/0287676 A1 | 11/2010 | Seo |
| 2011/0179541 A1 | 7/2011 | Wright |
| 2012/0017480 A1 | 1/2012 | Shtainhorn |
| 2012/0195010 A1 | 8/2012 | Kurokawa |
| 2014/0007312 A1 | 1/2014 | Wright |

FOREIGN PATENT DOCUMENTS

| | | |
|---|---|---|
| EP | 0403201 | 12/1990 |
| FR | 2478361 | 9/1981 |
| GB | 1133106 | 11/1968 |
| WO | WO 1985-05265 | 12/1985 |
| WO | WO 2011-046508 | 4/2011 |

* cited by examiner

PROTECTIVE HEADGEAR AND OPTICAL-FILTER CARTRIDGE REMOVABLY MOUNTABLE THERETO

BACKGROUND

Optical filters, such as e.g. automatic darkening filters, are often provided on protective headgear (e.g., helmets, shields, visors, or the like), e.g. where protection from high intensity light is desired.

SUMMARY

In broad summary, herein is disclosed a protective headgear and an optical filter cartridge that is removably mountable thereto, and methods of removably inserting such a cartridge and removing such a cartridge. These and other aspects of the invention will be apparent from the detailed description below. In no event, however, should this broad summary be construed to limit the claimable subject matter, whether such subject matter is presented in claims in the application as initially filed or in claims that are amended or otherwise presented in prosecution.

BRIEF DESCRIPTION OF THE DRAWINGS

FIG. 8a shows the cartridge when mounted in place in the holder.

FIG. 8b shows the cartridge after having been slidably moved in a first direction.

FIG. 8c shows the cartridge after having been rotated and in position to be removed from the holder.

Figure 1:
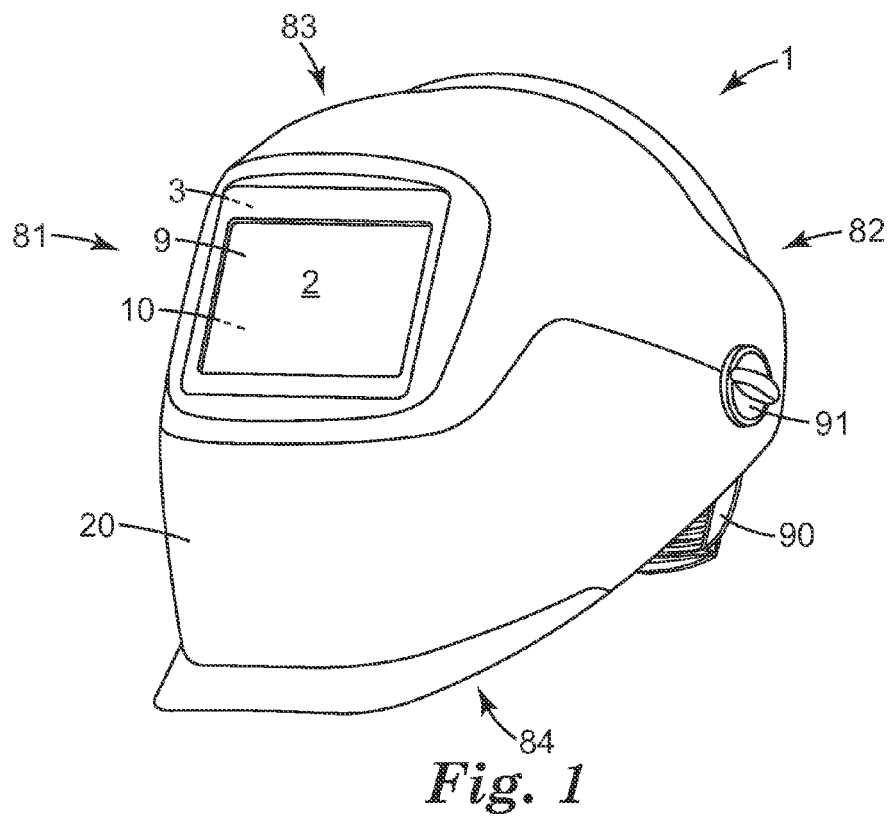
FIG. 1 is a front-side perspective view of an exemplary protective headgear comprising an exemplary optical-filter cartridge removably mounted thereto.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

DETAILED DESCRIPTION

Herein is disclosed a protective headgear 1 comprising an optical-filter cartridge 10 removably mountable thereinto, and methods of mounting and removing such a cartridge from such a headgear. In various embodiments, such a protective headgear may comprise e.g. a helmet, a shield, or a visor (e.g., a welding helmet, shield or visor), noting that there may not always be bright-line boundaries between protective headgear of these categories. As show in exemplary embodiment in FIGS. 1 and 2, protective headgear 1 comprises a main body 20 that (with headgear 1 as conventionally worn by a person) comprises a generally forward side 81, a generally rearward side 82, a generally upward or top side 83 (e.g., toward the crown of a wearer's head), and a generally bottom side 84 (e.g., toward the wearer's neck). Main body 20 comprises a generally forward-facing portion that comprises an optically-transmissive window 2. In many embodiments, optically-transmissive window 2 may take the form of a through-opening (as seen most easily in the exemplary embodiment of FIG. 6). As shown in exemplary embodiment in FIG. 3, protective headgear 1 comprises an optical-filter cartridge 10 that is mounted in headgear 1 as described in detail herein and that includes an optical-filtering lens 11 that is aligned with at least a portion of window 2 so that lens 11 can filter electromagnetic radiation (e.g., visible light, ultraviolet radiation, infrared radiation, etc.) that passes through window 2. That is, lens 11 is positioned within protective headgear 1 so that any electromagnetic radiation that reaches the eyes of a person wearing the headgear must first pass through lens 11 and so may be optically filtered in any desired manner.

Figure 3:
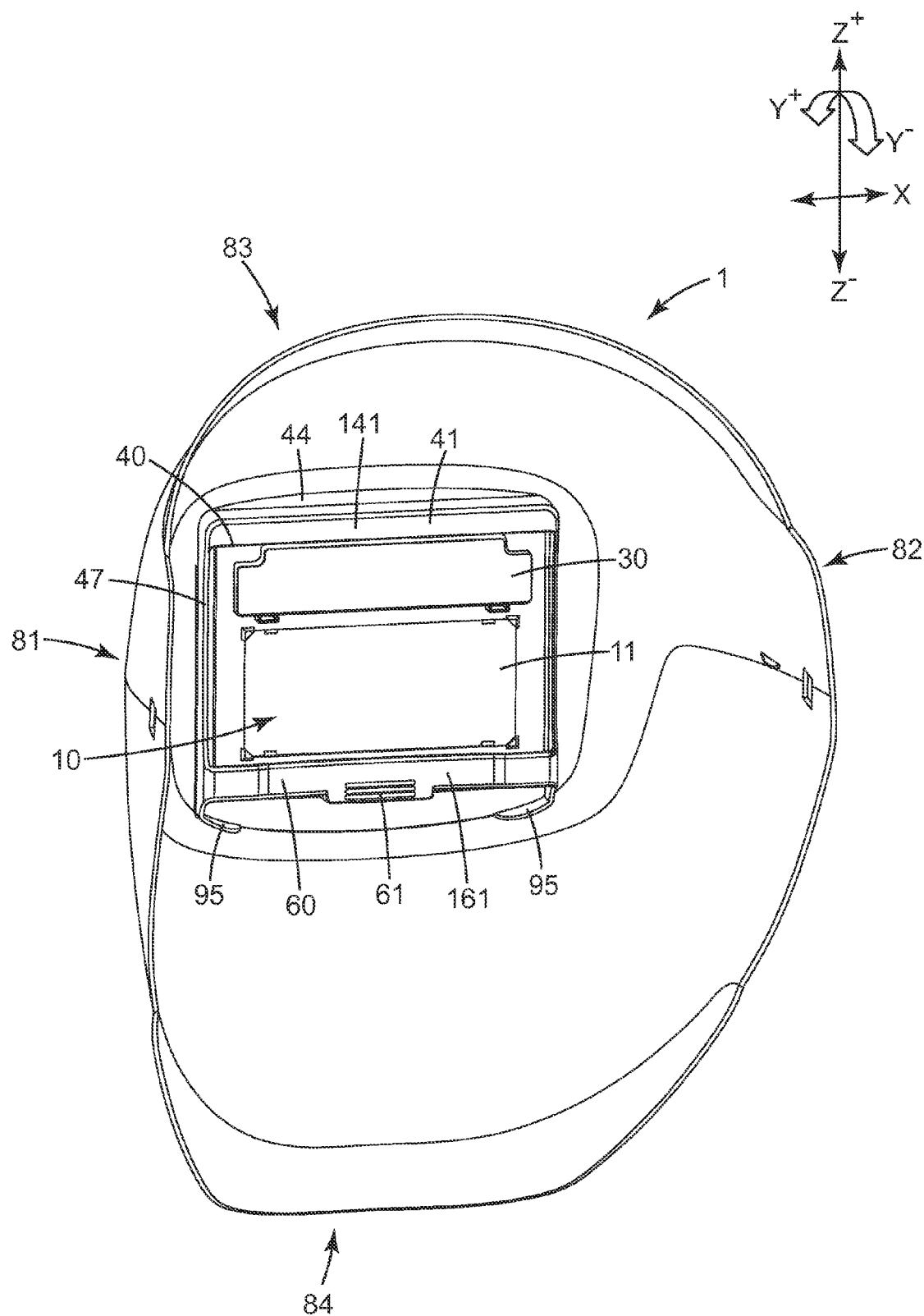
FIG. 3 is a rear-side perspective view of the exemplary protective headgear of FIG. 2, with the head suspension of the headgear omitted.
Figure 6:
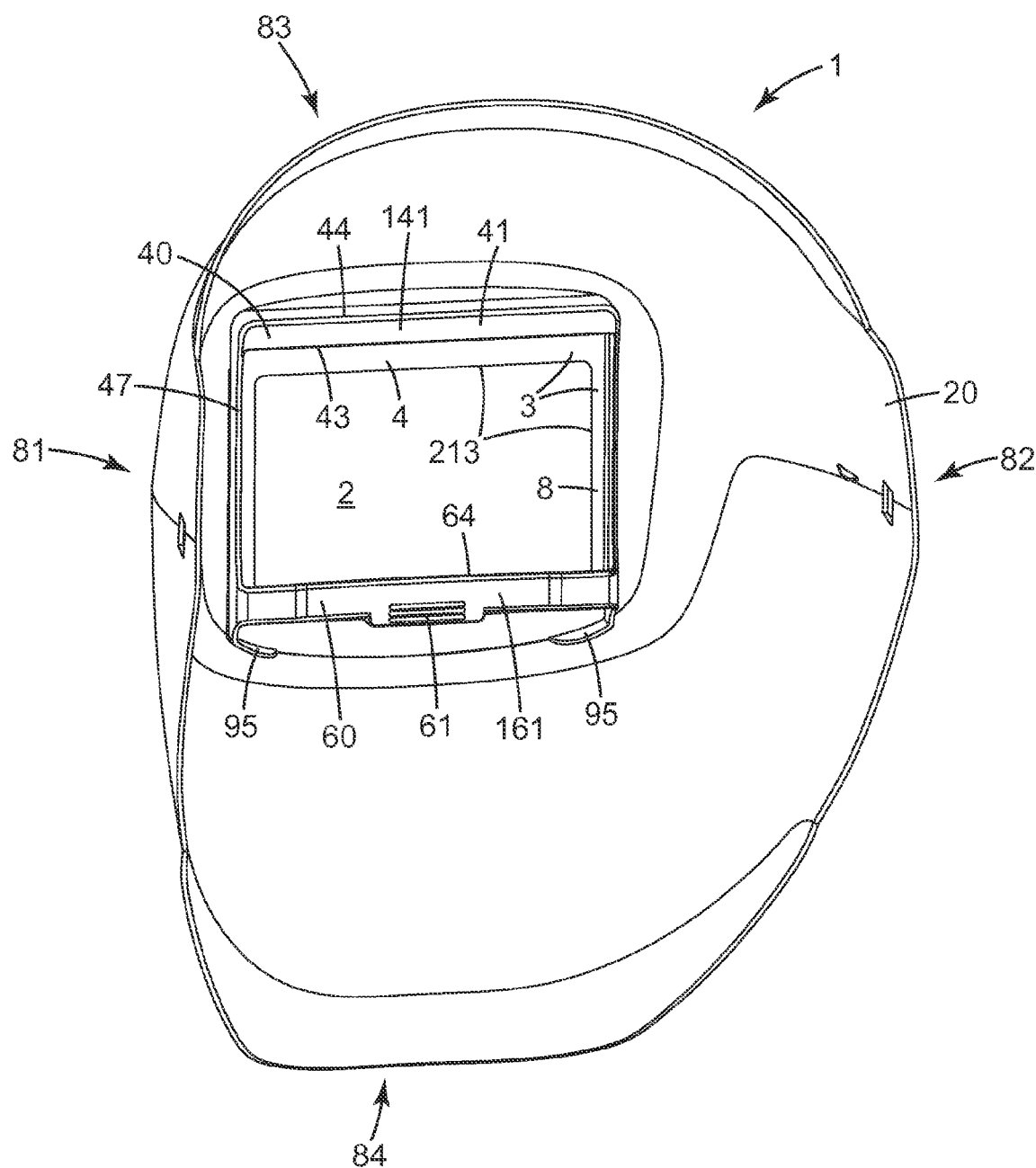
FIG. 6 is a rear-side perspective view of the exemplary protective headgear of FIG. 3, with the optical-filter cartridge omitted.

The removable mounting of cartridge 10 into headgear 1 is achieved by way of holder 40, as seen in exemplary representation in FIGS. 3 and 6 (with and without cartridge 10 mounted therein, respectively). The term holder refers to two or more components of headgear 1 that collectively removably hold cartridge 10 in place; it does not necessitate that the two or more components are portions of the same integral part or even that they must be directly connected to each other. In many embodiments, when cartridge 10 is removably mounted within headgear 1, portions (e.g., perimeter portions) of cartridge 10 may reside between various components of holder 40, and portions of a frame 3 that laterally surrounds window 2, as explained in detail herein.

Figure 2:
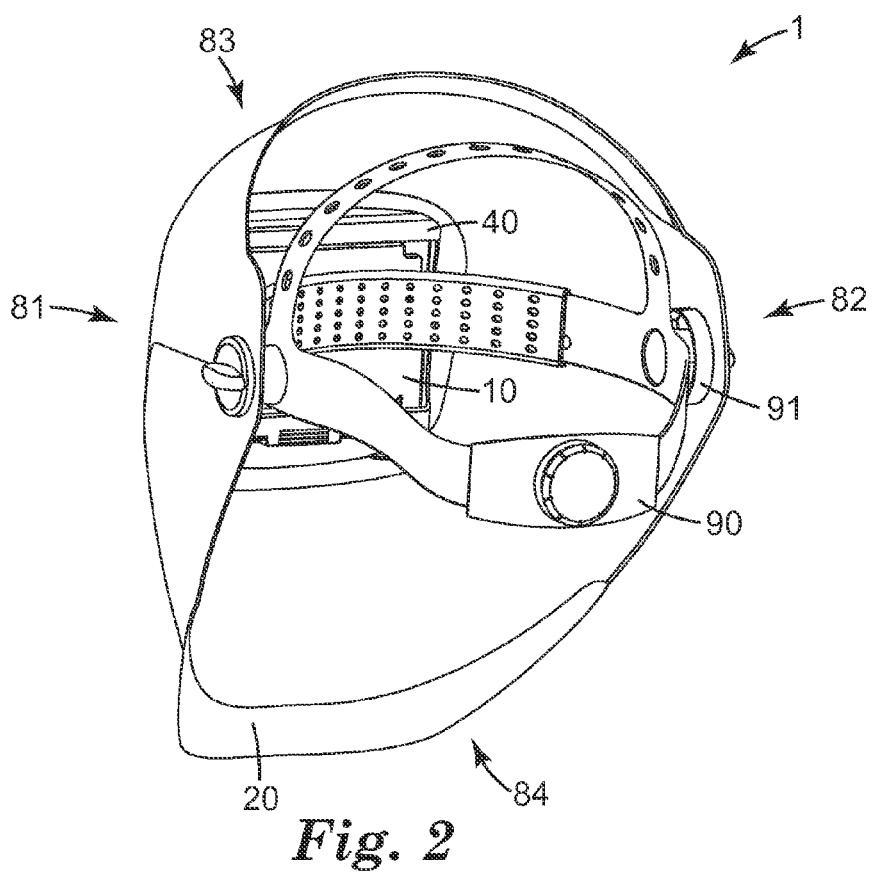
FIG. 2 is a rear-side perspective view of the exemplary protective headgear and optical-filter cartridge of FIG. 1.

For clarity of description, the following terminology is used:

With window 2 as a reference location, terms such as front, forward, etc. refer to a direction that is toward a source of electromagnetic radiation when headgear 1 is in use (thus for example, FIG. 1 is a view from the front side of headgear 1). Terms such as rear, rearward, etc., refer to a direction that is generally away from the front direction. The rear side of headgear 1 is thus the side that is configured to accept and optically shield at least a portion of a user's head (thus, FIGS. 2, 3 and 6 are views from the rear side of headgear 1).

These two directions thus combine to establish a forward-rearward axis and direction relative to window 2 of headgear 1.

As mentioned, headgear 1 comprises a frame 3 that laterally surrounds window 2. (While in many embodiments window 2 and/or frame 3 may conveniently be generally rectangular in shape, this is not strictly necessary, and either or both of these might be e.g. oval, or might at least have somewhat rounded corners.) By laterally is meant any direction that is generally orthogonal to the forward-rearward axis of window 2. By laterally inward is meant in a direction toward the lateral geometric center of window 2; by laterally outward is meant in a direction away from the lateral geometric center of window 2. By laterally surrounds is thus meant that frame 3 laterally-outwardly borders window 2 on all lateral sides of window 2. (In many embodiments, frame 3 may comprise laterally-inward edges 213 that define window 2, as in the exemplary embodiment depicted in FIG. 6.) Terms such as past or beyond (whether in a longitudinal direction or in a transverse direction, as discussed below) refer to a direction away from the geometric center of window 2.

With respect to cartridge 10, it will be appreciated from the disclosures herein that cartridge 10 may be inserted into holder 40, and removed therefrom, by steps that include rectilinear moving (e.g., sliding) cartridge 10 back and forth relative to window 2 and holder 40. With this in mind, the term longitudinal when used with respect to cartridge 10 refers to the direction/axis of rectilinear movement of cartridge 10. In the exemplary view of FIG. 4 (showing cartridge 10 in isolated side-rear view), the longitudinal direction of movement of cartridge 10 is indicated by the z axis. The transverse direction of cartridge 10 is the direction that is perpendicular to the longitudinal direction and that is generally in the same major plane as the longitudinal direction. Thus, in FIGS. 4 and 5, the transverse direction with respect to cartridge 10 is indicated by the X axis. The thickness direction and dimension of cartridge 10 is defined as the direction of cartridge 10 that is generally aligned with the forward-rearward axis of headgear 1 when cartridge 10 is mounted therein. Typically, the thickness dimension of cartridge 10 will be orthogonal to, and substantially smaller than, the longitudinal and transverse directions of cartridge 10.

With respect to holder 40, the longitudinal direction and axis of holder 40 (and window 2) denotes a lateral direction that is generally aligned, with certain limited deviations as discussed later herein, with the direction of rectilinear moving (e.g., sliding) of cartridge 10 back and forth relative to window 2 and holder 40. In the exemplary embodiment depicted in FIGS. 3 and 7, such a longitudinal direction with respect to holder 40 is indicated by the Z axis. Regarding these limited deviations, it will be explained in detail later herein that when cartridge 10 is in certain positions, a longitudinal axis Z of holder 40 and window 2 may be offset by an offset angle θ (theta), from a longitudinal axis z of cartridge 10.

First and second longitudinal ends of cartridge 10, window 2, frame 3, holder 40, etc., are those ends that are located along the respective longitudinal axis of that item (i.e., the z axis of the cartridge or the Z axis of the window, frame and holder). For example, in the exemplary embodiment depicted in FIGS. 3 and 6, the direction of rectilinear moving of cartridge 10 will be up and down relative to window 2 (and holder 40), therefore the top and bottom of window 2 as shown in these Figures are first and second longitudinal ends of window 2. The terminology of first end (whether of window 2, frame 3, holder 40, cartridge 10, etc.) denotes a longitudinal end to which a herein-described first retainer is proximal. The terminology of second end denotes a longitudinal end to which a second, deflectable retainer is proximal. The term transverse as applied to window 2, frame 3 and holder 40 denotes a lateral direction that is generally orthogonal to the longitudinal direction of window 2, frame 3 and so on. That is, in the view of FIG. 6, the left and right edges of window 2 will be transverse edges of window 2, sections 8 of frame 3 will be transverse sections of frame 3, and so on. In FIG. 3 and in other Figures, the transverse direction with respect to window 2, frame 3, holder 40, etc. is signified by the X axis (which axis will typically be aligned with the transverse axis x of cartridge 10).

The direction of slidable motion of cartridge 10 is dictated by the orientation of holder 40, so that the direction of rectilinear motion of cartridge 10 relative to frame 3 and headgear 1 may be altered by the design of holder 40. That is, in some embodiments holder 40 might be rotated 180 degrees relative to headgear 1, from the configuration shown in the Figures herein (i.e., it could be provided "upside down" from the configuration shown in FIG. 6). Alternatively, holder 40 might be rotated 90 degrees relative to headgear 1 (so that the direction of rectilinear motion of cartridge 10 might be "side-to-side" with respect to headgear 1 rather than "up and down"). In summary, the terminology of longitudinal, transverse, etc., is adopted herein purely for convenience in describing the moving of cartridge 10 relative to holder 40, and does not require any specific configuration of holder 40 and cartridge 10 relative to headgear 1. Furthermore, the designation of longitudinal and transverse directions and axes is with reference to the direction of rectilinear motion of cartridge 10 and does not require that a longitudinal dimension of any component must be longer than a transverse dimension of that component. In fact, in the specific embodiment shown in FIG. 4, the transverse dimension of cartridge 10 (i.e., its width along the X axis as shown) is greater than its longitudinal dimension (i.e., its up and down dimension along the z axis as shown).

As will be discussed, in certain steps of the methods disclosed herein, cartridge 10 may be (partially) rotated about a rotation axis that is proximal to one longitudinal end of cartridge 10 (i.e., so that the longitudinal end of cartridge 10 that is proximal to the rotation axis may rotate through a relatively smaller range of rotation, while the longitudinal end of cartridge 10 that is distal to the rotation axis may rotate through a relatively larger range of rotation). The direction of rotatably moving cartridge 10 about such a rotation axis is designated by the arcuate "axis" Y in e.g. FIGS. 3,4 and 5, with $Y^-$ (out-of-plane as viewed in FIGS. 3 and 4) indicating a movement in a rearward direction (away from frame 3) as defined above, and with $Y^+$ (into-plane as viewed in FIGS. 3 and 4) indicating a movement in a forward direction toward frame 3). At certain times and positions (i.e., when cartridge 10 is substantially parallel to window 2; e.g., at the start of rotating cartridge 10 away from being substantially parallel to window 2), rotation direction Y of cartridge 10 may substantially align with the forward-rearward axis of window 2. At other times and positions (i.e., after one longitudinal end of cartridge 10 has been rotated rearward away from window 2), such a rotation direction Y of cartridge 10 may diverge from such a forward-rearward axis of window 2, as will be appreciated later.

With these geometric terms and relationships having been presented, the structure and functioning of protective headgear 1 may now be discussed in various exemplary embodiments. As most easily seen in the exemplary embodiment of FIG. 6 (with cartridge 10 omitted), main body 20 of protective headgear 1 may comprise rear-facing frame 3, which laterally surrounds (and in some embodiments may define) window 2. As can be best seen in the isolated view of FIG. 7 (again with cartridge 10 omitted), in at least some embodiments frame 3 may be a generally planar frame that is provided by a generally flat area (shown stippled in FIG. 7) that surrounds window 2 and that comprises a rearward-facing surface 113 near and/or against which a forward-facing surface 25 of perimeter section 18 of cartridge 10 (which surface 25 and section 18 of cartridge 10 are shown e.g. in FIGS. 4 and 5) may be held, when cartridge 10 is mounted in position rearwardly adjacent window 2 and within holder 40. Such a frame might be provided e.g. by molding a flat area directly into main body 20 of protective headgear, which flat area borders and defines window 2 (as in the exemplary embodiment of FIGS. 6 and 7). Or, such a frame might be provided by a separately-made frame that is then attached to main body 20.

Figure 7:
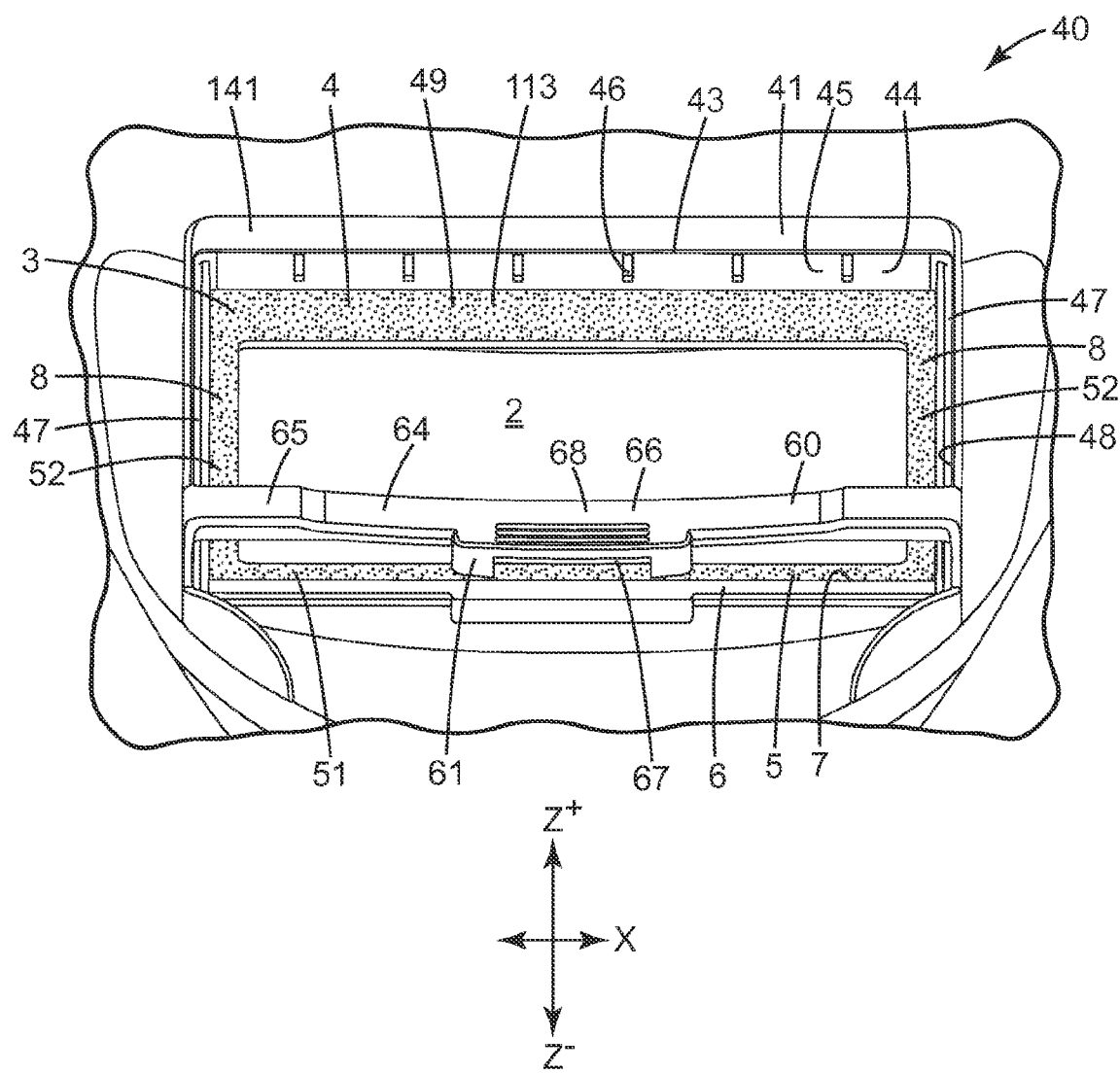
FIG. 7 is a rear-bottom perspective view of an exemplary holder for an optical-filter cartridge.

In the exemplary embodiment of FIGS. 6 and 7, frame 3 comprises first-end section 4 at a first longitudinal end of frame 3 (with first retainer 141 located proximal thereto), second-end section 5 at a second longitudinal end of frame 3 (with second, deflectable retainer 161 located proximal thereto), and transverse-side sections 8. Sections 4, 5 and 8 of frame 3 respectively comprise major rearward-facing surfaces 49, 51, and 52, as seen most easily in FIG. 7, which surfaces may combine to collectively provide major rearward-facing surface 113 of frame 3 referred to above. In the illustrated embodiment, first-end section 4 may be referred to as a top section of frame 3, second-end section 5 as a bottom section, and sections 8 as side sections (which top, bottom and side designations are with headgear 1 oriented as pictured in FIG. 6, i.e. in a conventional orientation with respect to a wearer's head). When cartridge 10 is mounted within holder 40, first-end section 22, second-end section 23, and transverse-side sections 24 of cartridge 10 (as seen e.g. in FIG. 4), may respectively be positioned rearwardly adjacent of first-end section 4, second-end section 5, and transverse-side sections 8 of frame 3.

Headgear 1 comprises holder 40 that comprises at least a first retainer 141 that is at a first longitudinal end of holder 40 as seen e.g. in FIGS. 6 and 7. First retainer 141 at least partially defines a first space that is between (in a forward-rearward direction) a portion of first retainer 141 and a portion of first-end section 4 of frame 3, which first space is configured to receive a first longitudinal end 12 of optical-filter cartridge 10. In at least some embodiments, first retainer 141 is a non-deflectable retainer. Holder 40 further comprises a second retainer 161 that is at a second longitudinal end of holder 40 that is longitudinally opposite the first longitudinal end of holder 40, again as seen e.g. in FIGS. 6 and 7. The first and second retainers of holder 40 combine to provide that when cartridge 10 is mounted in holder 40, cartridge 10 is prevented from slidably moving back and forth along longitudinal axis Z (as seen e.g. in FIG. 3). Thus in at least some embodiments, first retainer 141 comprises a first, longitudinal sidewall 44 that prevents cartridge 10 from moving longitudinally past sidewall 44 in the $Z^+$ direction as seen in FIG. 3. In some embodiments, sidewall 44 may comprise a forward base that is proximate surface 49 of first-end section 4 of frame 3, with sidewall 44 protruding generally rearwardly from its forward base. In various embodiments, sidewall 44 may be placed e.g. so that it longitudinally outwardly borders first-end section 4 of frame 3, and may comprise an elongate length that extends e.g. in a transverse direction. In the illustrated embodiment of FIG. 3, sidewall 44 takes the form of a continuous elongate wall. However, it is emphasized that this is not necessary and that sidewall 44 may be discontinuous if desired. For example, sidewall 44 might be collectively provided by a plurality of (e.g., two or more) posts or the like that extend generally rearwardly so as to block any longitudinal movement of cartridge 10 past them. If desired, sidewall 44 may comprise one or more struts or bumpers 46 that extend longitudinally inward therefrom, as seen in exemplary embodiment in FIG. 7. However provided, sidewall 44 or portions thereof may comprise a longitudinally inward-facing surface 45 near and/or against which a longitudinally-outward-facing surface 13 of first longitudinal end 12 of cartridge 10 may rest, when cartridge 10 is mounted in holder 40, e.g., as shown in representative manner in FIG. 8a (which is discussed in detail later). In embodiments in which cartridge 10 comprises a longitudinally-outermost lip 19 (as shown in exemplary illustration in FIG. 5), a longitudinally outermost surface of such a lip may provide the surface that resides near to and/or against surface 45 of sidewall 44). If desired, sidewall 44 may be shaped or contoured to accept a first end 12 of cartridge 10 of a particular shape.

In some embodiments, sidewall 44 may extend integrally from first-end section 4 of frame 3. In other embodiments, sidewall 44 may be a separate component that is attached to frame 3. In still other embodiments, in at least some locations, sidewall 44 may comprise a forward end that abuts surface 49 of first end section of frame 3, but is not attached to frame 3. In still other embodiments, in at least some locations, sidewall 44 may not approach near (e.g., within 0.5, 1, or 2 mm) surface 49 of frame 3, as long as at least some portions of sidewall 44 extend far enough toward frame 3 to prevent cartridge 10 from unacceptably longitudinally moving therebetween.

In some embodiments, first retainer 141 may further comprise a first member (e.g., a non-deflectable member) 41, which member can prevent first end 12 of cartridge 10 from rotatably moving rearward away from frame 3 (i.e., from moving in the $Y^-$ direction shown in FIG. 3). In some embodiments, first member 41 may take the form of a beam with an elongate extent that is e.g. generally aligned with a transversely-aligned elongate extent of first-end section 4 of frame 3. First member 41 may additionally be aligned with an elongate length of sidewall 44, as shown e.g. in FIG. 7. In some embodiments, sidewall 44 may be connected to first member 41 at least at some locations along an elongate length of sidewall 44 and of first member 41, e.g. so as to enhance the ability of member 41 to resist deflecting rearwardly.

In some embodiments, first member 41 may take the form of a generally continuous beam with a major plane that is oriented generally parallel to a major plane of first-end section 4 of frame 3. In the illustrated embodiment of FIGS. 3, 4 and 7, first member 41 takes the form of a continuous elongate flange that protrudes (from the rearward end of sidewall 44) longitudinally toward the second longitudinal end of holder 40. However, it is emphasized that this is not necessary and that member 41 may be discontinuous if desired. For example, member 41 might be collectively provided by a plurality (e.g., 2 or more) of members that are spaced along the transverse extent of the first end of holder 40. For example, such an arrangement may be provided e.g. by fingers, flanges or the like that are spaced along the transverse extent of the rearward end of sidewall 44 and that extend longitudinally therefrom.

Regardless of the specific design, it will be appreciated that in many embodiments it may be advantageous to provide that sidewall 44 protrudes rearwardly a distance that is at least as great as the thickness of optical-filter cartridge 10 at least at the first end 12 of cartridge 10 and at locations of the cartridge that are proximal thereto. It will be understood that this may ensure that sufficient forward-rearward space is provided between first member 41 and first-end section 4 of frame 3, to admit first end 12 of cartridge 10 thereinto. At least in such embodiments, first member 41 may comprise a forward-facing surface 42 near and/or against which a rearward-facing surface 21 of first longitudinal end 12 of cartridge may rest, when cartridge 10 is mounted in holder 40 (as shown e.g. in FIG. 8a).

Holder 40 further comprises second retainer 161 as mentioned above, which second retainer is by definition a deflectable retainer. This second, deflectable retainer 161 is at a second longitudinal end of holder 40 that is longitudinally opposite the first longitudinal end of holder 40 and that is proximate at least a portion of second-end section 5 of frame 3, as seen e.g. in FIGS. 6 and 7. Deflectable retainer 161 at least partially defines a second space that is between (in a forward-rearward direction) a portion of deflectable retainer 161 and a portion of second-end section 5 of frame 3, which second space is configured to receive a second longitudinal end 14 of optical-filter cartridge 10.

In at least some embodiments, second, deflectable retainer 161 comprises a second, deflectable member (e.g., beam) 60 with a long axis that is oriented generally orthogonally to longitudinal axis Z of window 2 and holder 40 (e.g., that is aligned with a transversely-extending elongate length of second-end section 5 of frame 3). A main body of deflectable member 60 may be rearwardly spaced away from second-end section 5 of frame 3, a distance that is at least as great as the thickness of optical-filter cartridge 10 at least at second end 14 of cartridge 10 and locations of cartridge 10 proximal thereto. Such a design can provide that sufficient forward-rearward space is provided between second member 60 and second-end section 5 of frame 3, to admit second end 14 of cartridge 10 thereinto. The main body of deflectable member 60 may comprise a forward-facing surface 63 near and/or against which a rearward-facing surface 21 of second longitudinal end 14 of cartridge may rest, when cartridge 10 is mounted in holder 40, as seen e.g. in FIG. 8a.

The deflectable member 60 can prevent second end 14 of cartridge 10 from rotatably moving rearward away from frame 3 when cartridge 10 is mounted within holder 40. In at least some embodiments, deflectable member 60 also comprises at least one retaining tab 61 (two such tabs are shown in FIGS. 3 and 7) that protrudes generally forwardly (i.e., toward second-end section 5 of frame 3) from a deflectable portion 68 of an elongate length of deflectable member 60. In various embodiments, such deflectable portion 68 may be centered at or near the middle of an elongate length of deflectable member 60. Retaining tab 61 may thus be positioned to prevent any longitudinal movement of second longitudinal end 14 of cartridge 10 past the second, deflectable member, when cartridge 10 is mounted within holder 40 (that is, when deflectable portion 68 is in the first, retaining position, tab 61 can prevent movement of cartridge 10 in the Z⁻ direction as depicted in the exemplary illustrations of FIGS. 7 and 8a).

As disclosed herein, deflectable portion 68 of second, deflectable member 60 may be forwardly and rearwardly deflectable (i.e., respectively toward, and away from, second-end section 5 of frame 3). This deflectability is between at least a first, forward position that is a retaining position in which retaining tab 61 is positioned (as described above) to prevent any longitudinally outward movement of second end 14 of cartridge beyond a predetermined distance past second, deflectable member 60; and, a second, rearward position that is a non-retaining position in which retaining tab 61 does not interfere with movement of second end 14 of cartridge 10 longitudinally outward toward or past second, deflectable member 60. In some embodiments, retaining tab 61 may comprise a longitudinally inward-facing surface 62 near and/or against which a longitudinally-outward-facing surface 15 of second longitudinal end 14 of cartridge 10 may rest, when cartridge 10 is mounted in holder 40 with deflectable portion 68 of member 60 in a forward, retaining position (as shown in exemplary illustration in FIG. 8a).

Figure 8A:
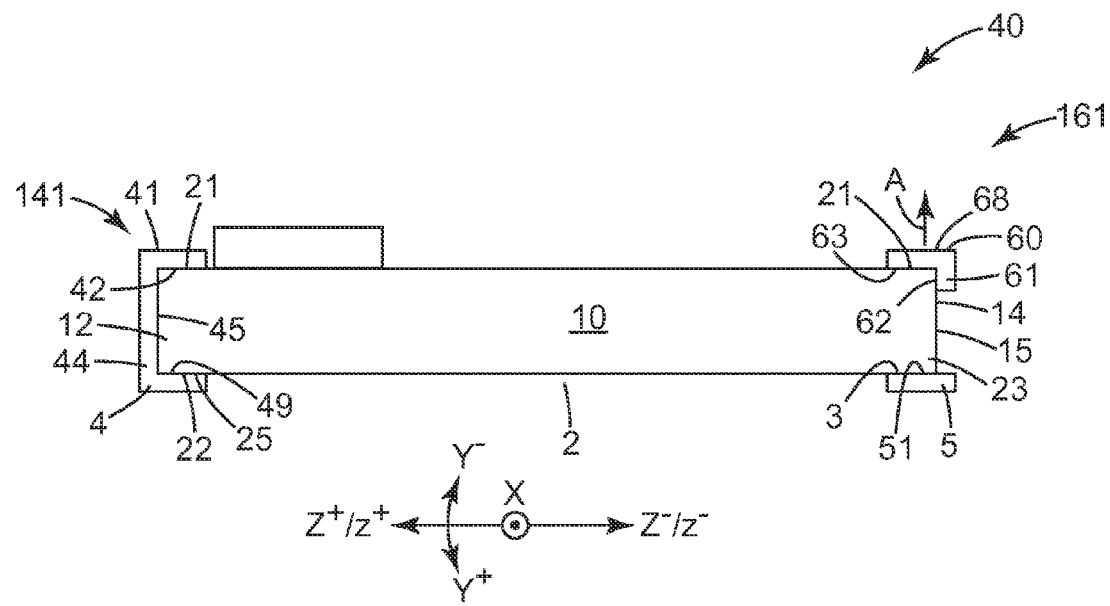
FIGS. 8a-8c are idealized side schematic cross-sectional exemplary views of a representative optical-filter cartridge in a representative holder and being removed from the holder.

In some embodiments, when cartridge 10 is mounted in holder 40 with deflectable portion 68 of member 60 in a forward, retaining position, substantially all of second end 14 of cartridge 10 may be positioned longitudinally inward from retaining tab 61 of member 60, as seen in FIG. 8a. In alternative embodiments, retaining tab 61, rather than fitting longitudinally outward of longitudinally-outward-facing surface 15 of second longitudinal end 14 of cartridge 10 as shown in FIG. 8a, may instead fit into a receptacle (e.g., a rearwardly-open-ended cavity) provided on rearward surface 21 of cartridge 10. In such embodiments, second longitudinal end 14 (or at least a portion thereof) of cartridge 10 may extend longitudinally outward past at least a portion of member 60 (and, in general, may extend past any portion of holder 40) a predetermined amount, when cartridge 10 is mounted in holder 40 with deflectable portion 68 of member 60 in a forward, retaining position.

It will be understood from the above description that the terminology that second retainer 161 is a deflectable retainer does not require the entirety of second retainer 161 be deflectable; it is only necessary that a portion thereof be flexible. It is further specified that deflectable denotes a component or a portion thereof that can be manually deflected (to a sufficient extent to perform the operations described herein) by hand; that is, by finger pressure, not requiring any sort of powered mechanism and not requiring the use of any sort of tool such as a screwdriver, pliers, pry bar, wrench, etc. (although such a tool could nevertheless be used if desired). In contrast, non-deflectable denotes a component or portion thereof that cannot be manually deflected by finger pressure to any significant extent (e.g. to allow removal of an optical-filter cartridge without having to deflect the second, deflectable retainer); or, cannot be so deflected without unacceptably damaging or destroying the component or portion thereof.

In some embodiments, first and second transverse ends of second, deflectable member (e.g., beam 60) may be connected to other portions of holder 40 (e.g. to any type of support, stanchion, buttress, wall, or the like) in such manner that the first and second transverse ends of member 60 are not deflectable. (In the exemplary embodiment depicted in FIG. 7, first and second transverse ends of member 60 are connected to transverse sidewalls 47.) In particular embodiments, such connection may be achieved by molding member 60 integrally with these other portions of holder 40 (e.g., the entirety of member 60 may be molded integrally with the entirety of holder 40).

In some embodiments, the second, retaining position of deflectable member 60 may be at or near its zero-force (equilibrium) position; that is, the position that member 60, and specifically the deflectable portion thereof, would assume in the absence of any deflecting force. Such an arrangement can provide that member 60 may be deflected rearward to its first, non-retaining position by the manual application of force by a user, and can then, at a desired time, be allowed to deflect forward toward its zero-force position. In some embodiments member 60 may be designed so that at least a slight forward bias is present within member 60, when it is in its second, retaining position. This may be achieved e.g. by setting the forward-rearward gap between second-end section 5 of frame 3 and member 60 (e.g., the "zero-force" gap as holder 40 is molded), to be very similar to, or even slightly less than, the thickness of cartridge 10 at its second end 14. With this in mind, it is noted that in herein-described embodiments in which forward-facing surface 63 of deflectable member 60 is rearwardly spaced away from surface 51 of second-end section 5 of frame 3, a distance that is at least about as great as a thickness of cartridge 10 at second end 14 of cartridge 10, the condition that such a distance is "at least about" as great is specially defined as meaning that the distance can be slightly less (i.e., up to 15% less) than the thickness of second 14 of cartridge 10. (Such a distance will of course be measured with deflectable member 60 in its zero-force position.)

The providing of a portion of member 60 with the ability to be deflected can be achieved with any suitable combination of the properties of the materials of member 60, and the geometric design of member 60. In some embodiments, such deflectability can be achieved by providing member 60 with an elongate length over which member 60 is not in contact with any other portion of second retainer 161 (or, in general, with any other part of holder 40) in such manner as would impede such deflection. In the illustrated embodiment most easily seen in FIG. 7, member 60 is an elongate beam that comprises a relatively long "free span" (over which it is not supported or contacted by any component of holder 40) that extends between the first and second transverse ends of member 60. That is, in such embodiments member 60 may be entirely unsupported except at its first and second transverse ends. Such support may be provided by sidewalls 47 as shown in the embodiment of FIG. 7, or by any other suitable support member.

The general approach of providing the desired deflectability at least partially by way of the geometric design of member 60, has significant advantages. Specifically, deflectable member 60 may not be required to be made of a particularly elastic material (although member 60 could be made of such material if desired). Thus, deflectable member 60 may be made of any suitable thermoplastic injection-molding material, including e.g. polypropylene, polyamide, and the like. (It is emphasized that these are non-limiting examples and any suitable molding material(s) may be used). Such molding materials may comprise any desired filler, additive, and so on, for any desired purpose, e.g. to enhance physical properties, to enhance flame-retardancy properties, and so on.

It will thus be appreciated that in various embodiments deflectable member 60 may be made of the same materials as, and may even be integrally made with (e.g. in the same molding process) and integrally connected thereto, any or all of the remaining components of second retainer 161, any or all of the components of holder 40, and even the main body 20 of protective headgear 1 (as well as any components that are integral with main body 20). Such arrangements may be much simpler and more cost-effective than e.g. making deflectable member 60 as a separate component that must be attached to the rest of second retainer 161, making second retainer 161 as a separate component that must be attached to the rest of holder 40, or making holder 40 as a separate component that must be attached to main body 20 of protective headgear 1. It will also be appreciated that it is unexpected that a single molding material may be used that provides main body 20 of protective headgear 1 with appropriate hardness, rigidity, impact resistance, etc., but that can also provide a deflectable member that is integrally molded with rigid and impact-resistant main body 20 but that nevertheless has sufficient deflectability to function as described herein.

In some embodiments, deflectable portion 68 of member 60 may comprise a reduced thickness and/or a reduced width (with the term width signifying a direction of the member that is generally aligned with the longitudinal axis of holder 40), in comparison to portions of member 60 that are proximate to the transverse ends of member 60. In the illustrated embodiment of FIG. 7, center portion 66 of elongate member 60 (which portion includes deflectable portion 68 and retaining tabs 61 thereof) has a reduced thickness in comparison to portions 65 of member 60. Any other approach, including e.g. the providing of cavities, through-openings, or the like, in center portion 66 of member 60 so as to e.g. enhance the ability of the portion of member 60 to be deflected, can be used. Since in many embodiments deflectable retainer 161 may be manually actuated (that is, one or more fingers of a person may provide the deflecting force to motivate deflectable portion 68 of deflectable member 60), if desired deflectable member 60 (e.g., deflectable portion 68 thereof) may comprise a feature (e.g., a notch 67 as seen in FIG. 7) to facilitate this manual actuation.

In at least some embodiments, second, deflectable retainer 161 may not comprise a longitudinal sidewall (the absence of such a longitudinal sidewall may be seen most easily in FIG. 7), so that upon deflection of second, deflectable retainer 161 from the first, retaining position, to the second, non-retaining position, second end 14 of cartridge 10 can be slidably moved longitudinally past second, deflectable retainer 161 (e.g., in the Z⁻ direction of FIGS. 3 and 7) in the process of inserting cartridge 10 within holder 40 and/or the process of removing cartridge 10 from within holder 40, as discussed in detail later herein.

In some embodiments, holder 40 may comprise transverse sidewalls 47, as seen most easily in FIG. 7. In some embodiments, such transverse sidewalls may provide support for a second, deflectable member 60 and/or a first member 41 as discussed herein. Such transverse sidewalls may also prevent cartridge 10 from moving transversely beyond sidewalls 47 (e.g., in the X direction of FIG. 3) when cartridge 10 is mounted in holder 40. That is, transverse sidewalls 47 can combine with first longitudinal sidewall 44 of first retainer 141 and with e.g. retaining tab 61 of second retainer 161 to hold cartridge 10 in its mounted position within holder 40 (without cartridge 10 unacceptably sliding around in any lateral direction). In such embodiments, transversely-outward-facing surfaces 17 of transverse sides 16 of cartridge (as seen e.g. in FIGS. 4 and 5) may reside near to and/or in contact with transversely-inward-facing surfaces 48 of transverse sidewalls 47.

Transverse sidewalls 47 may also assist in guiding cartridge 10 when it is moved longitudinally back and forth in the act of inserting or removing cartridge 10 as described later herein. In specific embodiments, transverse sidewalls 47 may be positioned transversely outward from transverse-side sections 8 of frame 3, and may comprise an elongate length that is oriented generally longitudinally. While the exemplary embodiment of FIG. 7 shows transverse sidewalls 47 as being continuous, any suitable design, including one in which a transverse sidewall is collectively provided by any suitable posts, protrusions, etc., can be used. However, a transverse sidewall should not comprise any portion that unacceptably prevents rectilinear or rotational movement of cartridge 10 generally rearward, away from frame 3.

In some embodiments, protective headgear 1 may comprise an optical cover pane 9 that is disposable and replaceable. Such a cover pane may be positioned e.g. forward of optical-filter cartridge 10 and rearward of rear-facing frame 3, so that a laterally outwardmost border portion of optical cover pane 9 lies in between optical-filter cartridge (specifically, perimeter section 18 thereof) and frame 3. Thus in such cases, forward-facing surface 25 of cartridge perimeter section 18 may rest against a major surface of optical cover pane 9 rather than resting directly against rearward-facing surface 113 of frame 3. In the event that window 2 of protective headgear 1 is a through-opening, a forwardmost surface of optical cover pane 9 may provide the forwardmost, exposed surface of the optical transmission path (e.g., as shown in FIG. 1). Such an optical cover pane may serve to protect optical-filter cartridge 10, and may be easily disposed and replaced with a fresh optical cover pane in the event that the cover pane becomes dirty, damaged, etc. Cover pane 9 may be made of any suitable material, e.g. polycarbonate, safety glass, and so on.

If such a cover pane is used, frame 3 and holder 40 may be designed to facilitate the secure holding, and easy removal when desired, of the cover pane. In one exemplary approach, second-end section 5 of frame 3 can be provided with a longitudinally-positioned (e.g., transversely extending) ledge 6 (as seen most easily in FIG. 7). Such a ledge may protrude rearwardly at least far enough to prevent longitudinal movement of a cover pane 9 beyond a desired point. Thus, once a cover pane 9 is placed in position against frame 3, it may be longitudinally held between longitudinally inward-facing surface 7 of ledge 6 at one longitudinal end, and longitudinal sidewall 44 at the other. It may similarly be transversely held between transverse sidewalls 47. Thus, when cartridge 10 is in place, cover pane 9 may be securely held in place so that it cannot be removed unless cartridge 10 is first removed. Once cartridge 10 is removed, cover pane 9 may be easily removed e.g. without requiring any additional manipulation of second, deflectable retainer 161.

It will be appreciated that the methods of removing and inserting optical-filter cartridge 10 disclosed herein are not limited to the specific circumstance of replacing an optical-filter cartridge. Rather, cartridge 10 may be removed in order to facilitate the replacing of an optical cover pane. Or, e.g. in the event that a protective headgear becomes damaged or otherwise unusable, a cartridge 10 may be removed from that protective headgear and placed into another protective headgear. It will also be appreciated that although components such as transverse sidewalls 47, ledge 6, and the like, have been described for convenience herein as being components of holder 40, such components do not necessarily have to be integrally connected to other components of holder 40 or even attached thereto. For example, if the first and/or second retainers are made as a separate module that is then attached to main body 20 of headgear 1, transverse sidewalls 47 might be provided as part of this separate module; or, sidewalls 47 might be molded into the main body of headgear 1 and can then act as part of finished holder 40 upon attachment of the separate module to the protective headgear to form holder 40. In addition, it will be appreciated that the various components (e.g., first and second retainers, etc.) may be in direct contact with a portion of main body 20 of protective headgear 1; or, they may be separated therefrom e.g. by one or more gaskets, protective layers, seals, cushions, or the like). Any components of holder 40 that are made separately and then attached to main body 20, can be so attached by any suitable method, including e.g. adhesive attachment, ultrasonic welding, solvent welding, mechanical fastening (by way of any suitable mechanical fastener, e.g. one or more screws, rivets, clips, and so on).

Figure 8B:
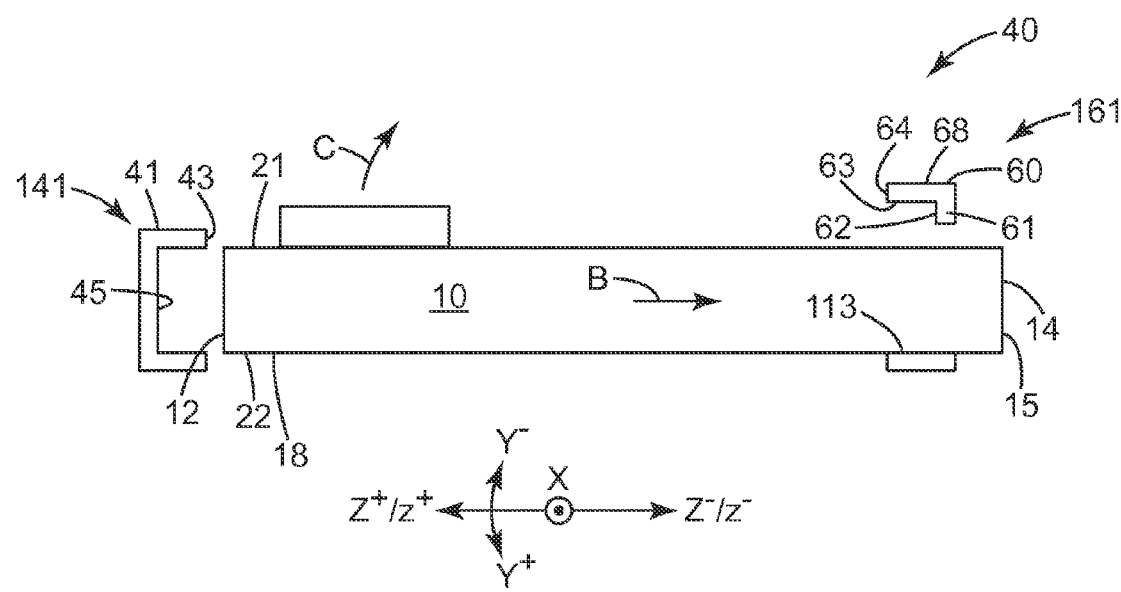
Figure 8C:
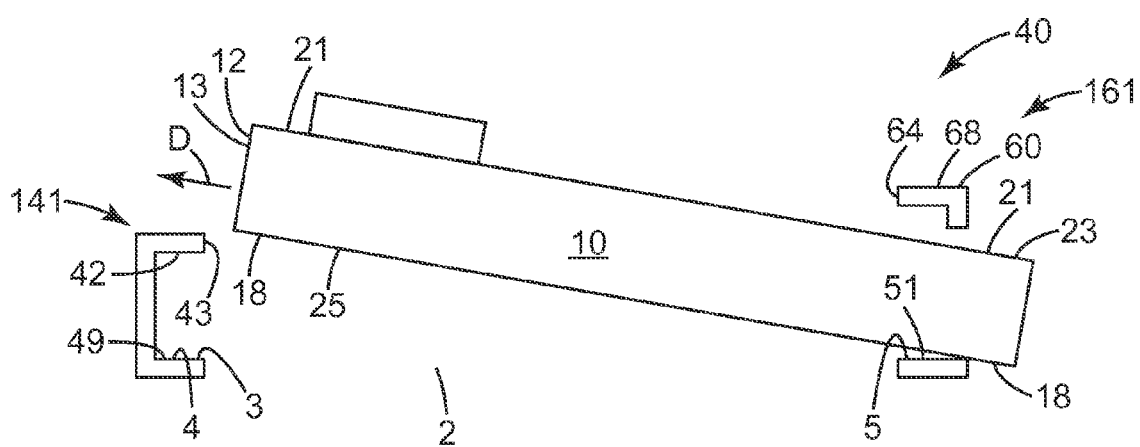
Figure 8C:
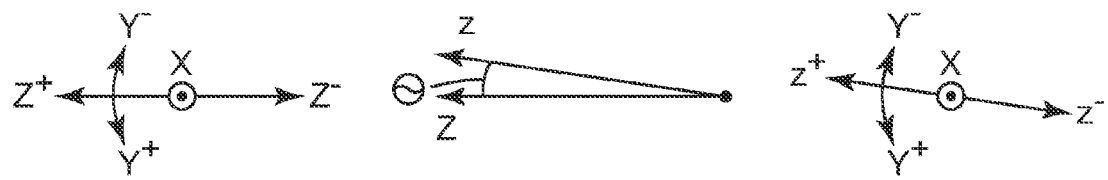

With the structure of the various components of protective headgear 1 having been described in detail, the use of such components to securely hold an optical-filter cartridge 10 within protective headgear 1, and yet to allow cartridge 10 to be quickly and easily removed if desired, will now be discussed. Methods of removing, and inserting, cartridge 10 from holder 40 will be discussed with respect to FIGS. 8*a*, 8*b*, and 8*c*. It is emphasized that FIGS. 8*a*, 8*b* and 8*c* are simplified, generic representations of a cartridge 10 and a holder 40 in side schematic cross-sectional view (an upward direction in these views corresponds to the previously-described rearward direction with respect to frame 3 and headgear 1). Thus, in FIGS. 8*a*-8*c*, similar reference numbers are used for various components of holder 40 and cartridge 10 as are used in other Figures, but it is understood that in FIGS. 8*a*-8*c* many such components are not shown in the exact exemplary embodiments pictured in the other Figures; and, several components are omitted for clarity.

In FIG. 8*a*, cartridge 10 is mounted within holder 40, with the cross-sectional viewing slice being is taken through deflectable portion 68 of deflectable member 60 of second, deflectable retainer 161, which retainer is in its first, forward (retaining) position. Cartridge 10 is longitudinally held between first and second retainers 141 and 161. In this position, first sidewall 44 of first retainer 141 prevents first end 12 of cartridge 10 from moving longitudinally therepast in the $Z^+$ direction; and, retaining tab 61 of second retainer 161 prevents second end 14 of cartridge 10 from moving longitudinally therepast, in a direction (the $Z^-$ direction) that is opposite the direction of movement prevented by first sidewall 44. In this manner cartridge 10 may be prevented from any significant longitudinal movement along the Z axis until such movement is desired. (Although not shown in FIG. 8*a*, transverse sidewalls may likewise prevent any significant transverse movement of cartridge 10).

Still as shown in FIG. 8*a*, cartridge 10 is positioned rearward of frame 3 (which frame laterally surrounds window 2); first end 12 of cartridge 10 is positioned forward of first member 41 of first retainer 141, and second end 14 of cartridge 10 is positioned forward of second, deflectable member 60 of second, deflectable retainer 161. In this manner cartridge 10 may be prevented from any significant forward-rearward movement (relative to window 2 and frame 3) until such movement is desired.

In some embodiments of the general configuration shown in FIG. 8*a*, forward-facing surface 25 of first-end section 22 of cartridge 10 may be near to and/or in contact with rearward-facing surface 49 of first-end section 4 of frame 3. Similarly, forward-facing surface 25 of second-end section 23 of cartridge 10 may be near to and/or in contact with rearward-facing surface 51 of second-end section 5 of frame 3. (Similarly, forward-facing surfaces 52 of transverse-side sections 24 of cartridge 10 may likewise be near to and/or in contact with transverse-side sections 8 of frame 3, although not shown in FIG. 8*a*.) However, as has been mentioned, in many embodiments an optical cover pane 9 (not shown in FIG. 8*a*) may be present between cartridge 10 and frame 3. In such embodiments, a forward-facing surface of cover pane 9 may be near to and/or in contact with the rearward-facing surface of frame 3, and a rearward-facing surface of cover pane 9 may be near to and/or in contact with the forward-facing surface of cartridge 10.

The moving of cartridge 10 can now be described, with reference to the various axes and directions shown in FIGS. 8a-8c. In these Figures, The Z axis is the longitudinal axis with reference to window 2/holder 40; the z axis is the longitudinal axis with reference to cartridge 10. In FIGS. 8a and 8b, these two axes are aligned; but this will not be true in FIG. 8c, as will be evident later. The X axis (in and out of the plane of FIGS. 8a-8c) is the transverse axis with reference to both window 2/holder 40 and cartridge 10. The Y axis represents the direction of (partial) rotation of cartridge 10.

To remove cartridge 10 from within holder 40, deflectable portion 68 of second, deflectable retainer 161 is manually deflected rearward (as indicated by arrow A of FIG. 8a) from a first, forward position as shown in FIG. 8a, to a second, rearward position as shown in FIG. 8b. The second position is a non-retaining position in which second, deflectable retainer 161 (e.g., retaining tab 61 thereof) no longer prevents longitudinally outward movement of second end 14 of cartridge 10. While second, deflectable retainer 161 is held in the second, non-retaining position, cartridge 10 can be slidably moved (as indicated by arrow B of FIG. 8b) longitudinally toward the second end of holder 40 (i.e., in direction $Z^-/z^-$ of FIGS. 8a and 8b). It will be appreciated that once deflectable member 60 has been deflected and cartridge 10 has begun moving toward the second end of holder 40, it may not be necessary to continue to apply manual (e.g., finger) pressure to maintain the member in its deflected condition during the remaining steps of the insertion or removal of the cartridge. Cartridge 10 can be moved a sufficient distance in the $Z^-/z^-$ direction that first end 12 of cartridge 10 is no longer prevented from moving generally rearward (away from frame 3) by any portion of first retainer 141 (specifically, by first member 41 of first retainer 141). Such a position is shown in FIG. 8b. However, cartridge 10 should not be moved so far that e.g. second end 14 of cartridge 10 might unacceptably impinge upon some portion of the main body of protective headgear 1, when the rotation step described below is carried out.

With cartridge 10 having been slidably moved to an appropriate position, cartridge 10 can now be rotated a suitable amount (as indicated by curved arrow C of FIG. 8b), with respect to an axis of rotation that is proximate second end 14 of cartridge 10. This rotation will be such that first end 12 of cartridge 10 moves in a generally rearward direction (i.e., along an arcuate path indicated by the $Y^-$ axis of FIG. 8b). The rotation is carried out until first end 12 of cartridge 10 has moved generally rearward relative to first retainer 141, far enough that cartridge 10 can then be moved generally toward the first end of window 2 (e.g., into the position of FIG. 8c) without being physically blocked by any part of first retainer 141. That is, the rotation should provide that subsequent movement of cartridge 10 generally toward the first end of window 2 does not cause first end 12 of cartridge 10 to impinge on first member 41 (e.g., upon longitudinally inwardmost tip 43 of first member 41) of first retainer 141.

This done, cartridge 10 may now be moved generally toward the first end of window 2, in the $z^+$ direction as indicated by arrow D of FIG. 8c. This process will remove second end 14 of cartridge 10 from being between second, deflectable retainer 161 and any portion of frame 3. That is, this movement will release cartridge 10 from holder 40 (e.g., so that cartridge 10 can be moved rearward away from frame 3 at will, without second end 14 of cartridge 10 impinging on longitudinally-inwardmost tip 64 of second, deflectable retainer 161). Once cartridge 10 has been removed, an optical cover pane 9 can now be easily removed if such a cover pane is present.

It will be appreciated that the angle over which cartridge 10 may be partially rotated may be advantageously designed. That is, cartridge 10 should be rotated far enough to provide the desired release of first end 12 of cartridge 10 from first retainer 141, but not so far as to impinge the second end 14 of cartridge 10 upon a portion of main body 20 of protective headgear 1 in such a manner as to damage the cartridge or the headgear, and not so far as to damage any portion of second retainer 161. Such rotating can be characterized in terms of the off-angle that it generates between longitudinal axis Z of holder 40, and longitudinal axis z of cartridge 10. Before any rotation, the Z and z axes will typically be aligned (e.g., as shown in FIGS. 8a and 8b). The rotation will then cause the z axis to be offset (rearwardly) from the Z axis, providing an off-angle θ as shown in FIG. 8c. Thus in various embodiments, the rotating, and the resulting off-angle θ between the longitudinal axis of cartridge 10 and the longitudinal axis of holder 40, may be at least 3, 5, 7, 9, 11, 13, or 15 degrees. In further embodiments, such an angle of rotation and resulting off-angle, may be at most about 45, 30, 25, 20, 15, or 13 degrees.

To removably insert a cartridge 10 into holder 40 (e.g., after the insertion of an optical cover pane 9 if desired), second, deflectable retainer 161 may be deflected into a second, non-retaining condition. With deflectable retainer 161 held in this non-retaining condition and with cartridge 10 held at an off-angle relative to the longitudinal axis of holder 40 (both as shown in FIG. 8c), cartridge 10 may be moved generally toward deflectable retainer 161 (i.e., moved in its $z^-$ direction) so that second end 14 of cartridge 10 passes into and at least partially through the space defined between second retainer 161 and second-end section 5 of frame 3. (This step is essentially the opposite of that indicated by arrow D of FIG. 8c). With cartridge 10 having been slidably moved to an appropriate position, cartridge 10 can then be rotated a suitable amount with respect to an axis of rotation that is proximate second end 14 of cartridge 10, such that first end 12 of cartridge 10 moves in a generally forward direction (along an arcuate path indicated by the $Y^+$ axis). (This step is essentially the opposite of that indicated by arrow C of FIG. 8b). The rotation can be continued e.g. until cartridge 10 is substantially aligned with holder 40, e.g. until the above-mentioned off-angle θ is essentially zero.

After this, cartridge 10 can be slidably moved in the $Z^+$ direction toward first retainer 141 (i.e., in the opposite direction as that indicated by arrow B of FIG. 8b) so that first end 12 of cartridge 10 enters the space between first retainer 141 and first-end section 4 of frame 3. As a consequence of this moving process, the second end 14 of cartridge 10 will move longitudinally inward relative to second, deflectable retainer 161 to the point that second, deflectable retainer 161 can be moved forwardly into its first, retaining position (i.e., in the opposite direction as that indicated by arrow A of FIG. 8a). At this point, cartridge 10 is now removably held within holder 40.

It will be appreciated that in some embodiments, upon the slidable moving of cartridge 10 toward the first end of the holder a sufficient amount, second, deflectable retainer 161 may deflect to its first, retaining position more or less automatically. (For example, once second end 14 of cartridge 10 is located longitudinally inward from retaining tab 61, an inherent bias of member 60 toward the first, retaining position may be sufficient to return member 60 toward or to the first, retaining position.) However, in some cases this deflecting of second, deflectable retainer 161 to its first, retaining position may be performed manually, or may be manually assisted, if desired.

In some embodiments, protective headgear 1 may comprise at least one auxiliary retainer (e.g., a non-deflectable retainer) 95 that is located longitudinally beyond second, deflectable retainer 161. Such an auxiliary retainer may prevent second end 14 of optical-filter cartridge 10 from moving longitudinally past auxiliary retainer 95. That is, such an auxiliary retainer may tend to limit the distance that cartridge 10 can move longitudinally beyond second retainer 161, to a predetermined amount. Two exemplary auxiliary retainers 95 are shown e.g. in FIGS. 3 and 6. Any suitable design and/or number of auxiliary retainers can be used. Of course, such auxiliary retainers may be located some distance away from the other components of holder 40 (e.g., from first and second retainers, transverse sidewall, etc.). In some embodiments, such auxiliary retainers may conveniently be integrally molded with main body 20 of protective headgear 1.

In some embodiments, protective headgear 1 may comprise a suspension 90, which may be attached to protective headgear 1 by an attachment mechanism 91, as shown e.g. in FIG. 2. Any such suspension may be used, and may comprise any suitable combination of e.g. brow bands, crown bands, occipital bands, and so on. In addition to such a suspension, one or more pads may be provided e.g. on the underside of the crown portion of headgear 1, which pads may serve a protective and/or cushioning function.

Optical-filter cartridge 10, and lens 11 thereof, may comprise any suitable device (whether active or passive) that is capable of suitably intercepting, blocking, filtering, etc., electromagnetic radiation. For example, optical-filter cartridge 10 may be capable of reducing high-intensity light as encountered in welding operations, to an intensity that is acceptable to a wearer of protective headgear 1. In specific embodiments, optical-filter cartridge 10 and lens 11 thereof may comprise a so-called automatic darkening filter in which lens 11 includes a switchable shutter that is capable of controllably blocking electromagnetic radiation (i.e., can switch between at least a light state (e.g. in which is it relatively highly light-transmissive) and a dark state (e.g. in which it is relatively non-transmissive to light)). Such a switchable shutter may comprise e.g. one or more liquid crystal layers, polarizing filters, electrochromic materials, etc., as are familiar to those of ordinary skill. If desired, other components (e.g. additives within layers of the shutter, and/or separate layers in the light path) may be provided that constantly block (whether by absorption, reflection, scattering, or some other mechanism) radiation of various wavelengths to a desired degree. For example, ultraviolet-blocking coatings, infrared-blocking coatings, interference filters, and the like, may be provided as part of lens 11 of cartridge 10.

In some embodiments, cartridge 10 may comprise a detector that is capable of detecting e.g. at least the presence of high intensity light, and may further comprise a shutter control system that receives input from the detector and controls the switchable shutter in response. Cartridge 10 may comprise an internal power supply (e.g., one or more batteries). However, it will be appreciated that any of these components or functionalities (e.g., detector, shutter control system, power supply, detector, and any items or functionalities associated therewith (e.g., wiring, connectors, status indicators, on/off switches and other controls, etc.)) may be located in a separate location (e.g., in a separate module of protective headgear 1) rather than being located on or within cartridge 10 itself.

Figure 4:
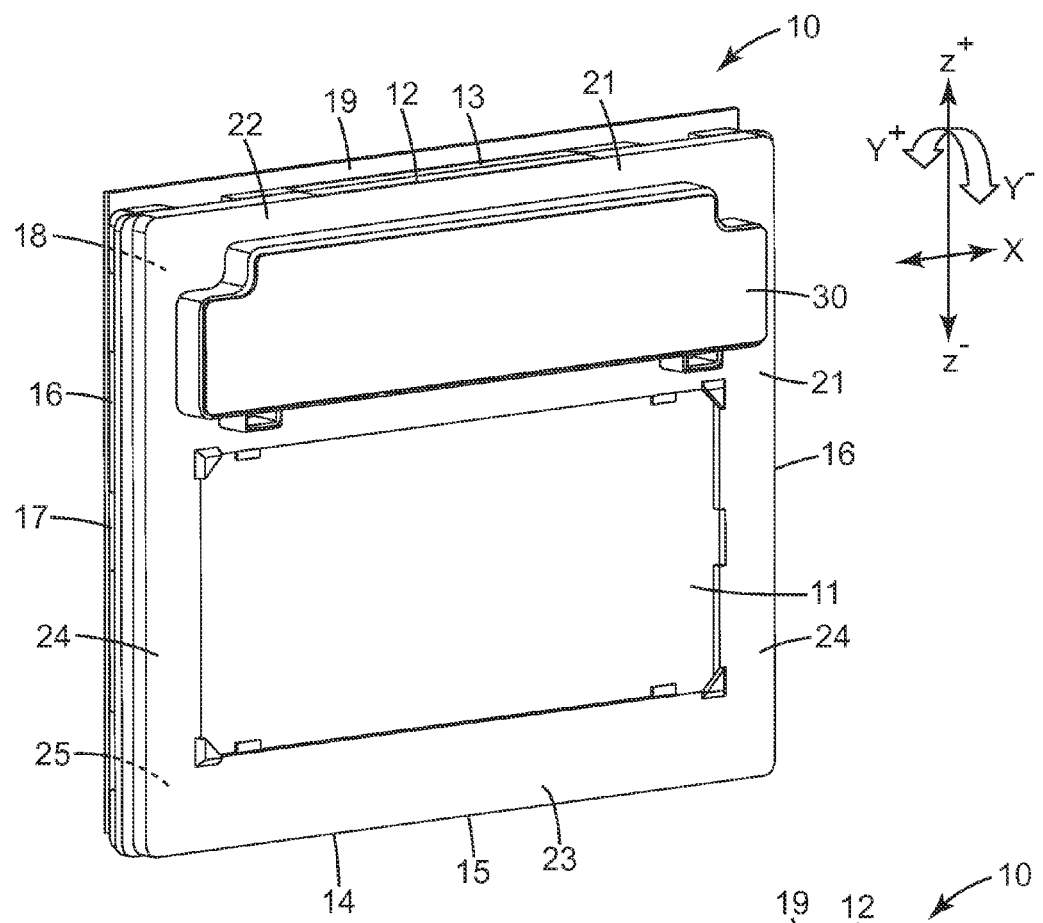
FIG. 4 is a rear-side perspective view of an exemplary optical-filter cartridge.
Figure 5:
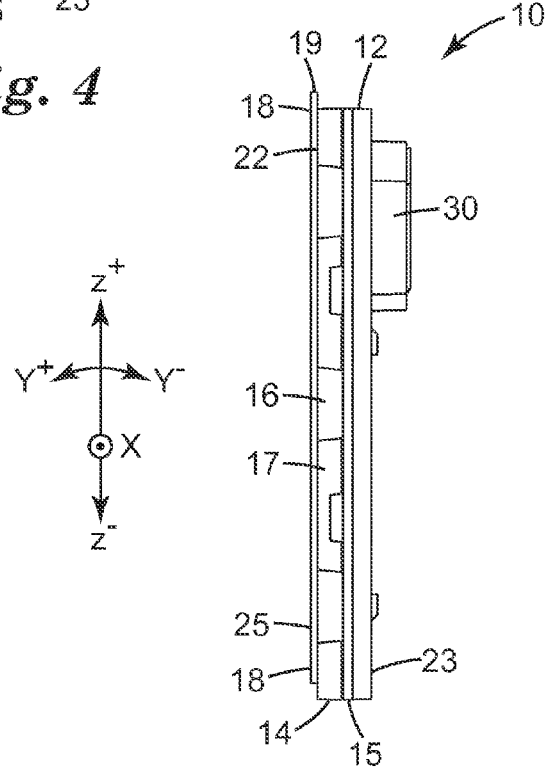
FIG. 5 is a side view of the exemplary optical-filter cartridge of FIG. 4.

In some embodiments, a portion of optical-filter cartridge may protrude rearwardly past e.g. part or all of first retainer 141 and/or part or all of second retainer 161, as long as such a portion does not interfere with the functionality described herein. For example, the exemplary cartridge 10 as shown in FIGS. 4 and 5 comprises module 30 (which may contain any desired component or perform any desired function), which module will not unacceptably interfere with the first end 12 of cartridge 10 from entering and residing in a space between e.g. member 41 of first retainer 141, and first-end section 4 of frame 3, as described herein.

It will be appreciated that the disclosures herein provide an apparatus and method for removably mounting an optical-filter cartridge within a main body of a protective headgear, that is simple and straightforward and requires a minimum of components (e.g., a minimum of movable parts). Accordingly, in some embodiments no other retainers (of any type, whether in the form of one or more clips, elastic bands, hooks, springs, wires, screws, rivets, hook and loop fasteners, etc.) are used to retain the optical-filter cartridge in place within the main body of the protective headgear except for the herein-described first retainer and second, deflectable retainer (and any transverse sidewalls if present). In some embodiments the first retainer does not comprise any movable parts; in some embodiments the second, deflectable retainer does not comprise any movable parts other than a deflectable portion of a deflectable member (e.g., beam) of the second, deflectable retainer. In a specific embodiment, a deflectable portion of a deflectable member of the second, deflectable retainer is the only movable part associated with the removable mounting of an optical-filter cartridge in the main body of the protective headgear (not counting the cartridge itself or any optical cover pane used therewith).

Protective headgear 1 may be used e.g. in connection with industrial operations, for example welding (e.g. arc welding, torch welding, acetylene welding), cutting (e.g. laser cutting, acetylene cutting), brazing, soldering, grinding, and the like. It may also be used in connection with medical procedures involving high intensity light (e.g. laser surgery, hair removal, tattoo removal, light-curing of dental resins, etc.). Many other uses are possible.

LIST OF EXEMPLARY EMBODIMENTS

Embodiment 1

A protective headgear for use with an optical-filter cartridge that is removably mountable in the protective headgear, the protective headgear comprising: a main body comprising a forward-facing portion with an optically transmissive window, a rear-facing frame that laterally surrounds the window and that comprises a longitudinal direction and a transverse direction and that comprises a first-end section and a second-end section, at first and second, longitudinally-opposite ends of the frame; and, a first retainer that is attached to the main body at a location proximate the first-end section of the frame, which first retainer comprises a rearward portion that at least partially defines a first space that is between at least a part of the rearward portion of the first retainer and at least a part of the first-end section of the frame, which first space is configured to receive a first end of an optical-filter cartridge; and, a second, deflectable retainer that is attached to the main body at a location proximate the second-end section of the frame, which second, deflectable retainer comprises a rearward portion that at least partially defines a second space that is between at least a part of the rearward portion of the second, deflectable retainer and at least a portion of the second-end section of the frame, which second space is configured to receive a second end of the optical-filter cartridge.

Embodiment 2

The protective headgear of embodiment 1 wherein the first retainer comprises a first, longitudinal sidewall with a forward base that is proximate a surface of the first-end section of the rear-facing frame, which first sidewall protrudes generally rearwardly from the forward base of the first sidewall.

Embodiment 3

The protective headgear of embodiment 2 wherein the first sidewall protrudes generally rearwardly from the forward base of the first sidewall, a distance that is at least as great as a thickness of the optical-filter cartridge at the first end of the optical-filter cartridge.

Embodiment 4

The protective headgear of any of embodiments 2-3 wherein the first retainer is a non-deflectable retainer, in which the rearward portion of the first retainer comprises a first, non-deflectable beam that comprises an elongate extent that is generally aligned with a transversely-aligned elongate extent of the first-end section of the frame.

Embodiment 5

The protective headgear of embodiment 4 wherein the first sidewall comprises an elongate extent that is generally aligned with a transversely-aligned elongate extent of the first-end section of the frame, and wherein at some location along the elongate extent of the first sidewall, the first sidewall is connected to the first, non-deflectable beam, so as to enhance the ability of the beam to resist deflecting rearwardly.

Embodiment 6

The protective headgear of embodiment 5 wherein the first sidewall protrudes generally rearwardly from the forward base of the first sidewall to a rearward end of the first sidewall, and wherein the first, non-deflectable beam is provided by a flange that extends from the rearward end of the first sidewall, in a direction that is generally longitudinally toward the second end of the frame.

Embodiment 7

The protective headgear of any of embodiments 1-6 wherein the second, deflectable retainer comprises a second, deflectable beam with a long axis that is generally aligned with the transverse direction of the frame and that is generally parallel to a major plane of the second-end section of the frame.

Embodiment 8

The protective headgear of embodiment 7, and wherein the second, deflectable beam is rearwardly spaced away from the second-end section of the frame so that when the second, deflectable beam is in a zero-force condition, a distance from a forward-facing surface of the second, deflectable beam to a surface of the second-end section of the frame, is at least about as great as a thickness of the optical-filter cartridge at the second end of the optical-filter cartridge.

Embodiment 9

The protective headgear of any of embodiments 7-8 wherein the second, deflectable beam comprises a deflectable portion that is forwardly and rearwardly deflectable between a first, forward position that is a retaining position in which a retaining tab that protrudes generally forwardly from the second, deflectable beam toward the second-end section of the frame, is positioned to prevent any longitudinally outward movement of the second end of the optical-filter cartridge beyond a predetermined distance past the second, deflectable beam; and, a second, rearward position that is a non-retaining position in which the retaining tab does not interfere with longitudinally outward movement of the second end of the optical-filter cartridge.

Embodiment 10

The protective headgear of embodiment 9 wherein the second, deflectable beam comprises an elongate length and wherein the deflectable portion of the second, deflectable beam is located generally proximate the middle of the elongate length of the second, deflectable beam; and, wherein first and second transverse ends of the second, deflectable beam are connected to other portions of the second, deflectable retainer so that first and second transverse end portions of the elongate beam are not deflectable.

Embodiment 11

The protective headgear of any of embodiments 7-10 wherein the second, deflectable beam comprises a free span over which the second, deflectable beam is not in contact with any other portion of the second, deflectable retainer, which free span is longer than a transverse width of the optical-filter cartridge.

Embodiment 12

The protective headgear of any of embodiments 7-11 wherein at least the second, deflectable beam of the second, deflectable retainer is made of the same material as other components of the second, deflectable retainer and is integrally molded therewith.

Embodiment 13

The protective headgear of any of embodiments 1-12 wherein the second, deflectable retainer is made of the same material as the first retainer and is integrally molded therewith.

Embodiment 14

The protective headgear of any of embodiments 1-13 wherein the second, deflectable retainer and the first retainer are made of the same material as the main body of the protective headgear and are integrally molded therewith.

19

Embodiment 15

The protective headgear of any of embodiments 1-14 wherein the second, deflectable retainer does not comprise a longitudinal sidewall, so that upon deflection of the second, deflectable retainer from the first, retaining position, to the second, non-retaining position, the second end of the optical-filter cartridge can be slidably moved longitudinally outward past the second, deflectable retainer.

Embodiment 16

The protective headgear of any of embodiments 1-15, further comprising at least one auxiliary retainer that is located longitudinally beyond the second, deflectable retainer, and that prevents the second end of the optical-filter cartridge from moving longitudinally outward past the auxiliary retainer.

Embodiment 17

The protective headgear of any of embodiments 1-16, further comprising a first transverse sidewall that prevents any movement of any portion of the optical-filter cartridge transversely outward past the first transverse sidewall; and, a second transverse sidewall that prevents any movement of any portion of the optical-filter cartridge transversely outward past the second transverse sidewall in a direction generally opposite the direction of movement prevented by the first transverse sidewall, wherein the first and second transverse sidewalls are made of the same material as the second, deflectable retainer and the first retainer and the main body of the protective headgear, and are integrally molded therewith.

Embodiment 18

The protective headgear of any of embodiments 1-17, comprising an optical-filter cartridge that is removably mounted in the main body of the protective headgear by way of being positioned rearwardly adjacent the rear-facing frame and held in that position by the first retainer and the second, deflectable retainer.

Embodiment 19

The protective headgear of embodiment 18, further comprising an optical cover pane that is disposable and replaceable and that is positioned forward of the optical-filter cartridge and rearward of the rear-facing frame, so that a laterally outwardmost border of the optical cover pane is in between a perimeter portion of the optical-filter cartridge and at least a portion of the frame.

Embodiment 20

The protective headgear of embodiment 19, wherein when the optical cover pane is in position between the optical-filter cartridge and the frame, the optical cover pane has a first longitudinal end that abuts a longitudinal sidewall of the first retainer; and, wherein the second-end portion of the frame comprises a rearwardly-protruding ledge, which ledge comprises a longitudinally-inward-facing surface that abuts a second longitudinal end of the optical cover pane when the optical cover pane is in position between the optical-filter cartridge and the frame.

20

Embodiment 21

The protective headgear of any of embodiments 1-20, wherein no other retainers are used to retain the optical-filter cartridge in place within the main body of the protective headgear except for the first retainer and the second, deflectable retainer; wherein the first retainer does not comprise any movable parts; and, wherein the second, deflectable retainer does not comprise any movable parts other than the deflectable portion of a deflectable beam of the second, deflectable retainer.

Embodiment 22

The protective headgear of any of embodiments 1-21 wherein the protective headgear is a welding helmet, shield or visor.

Embodiment 23

A method of removing an optical-filter cartridge from a holder of a protective headgear, the method comprising: deflecting a second, deflectable retainer that is at a second end of the holder, from a first position into a second, non-retaining position in which the second, deflectable retainer does not prevent longitudinally outward movement of a second end of the cartridge; slidably moving the cartridge generally longitudinally toward the second end of the holder so as to move a second end of the cartridge longitudinally outward past the second, deflectable retainer and so as to move a first end of the cartridge longitudinally inward out of a space that is partially defined by a first retainer at a first end of the holder; then, rotating the cartridge about a rotation axis that is proximate the second end of the optical-filter cartridge so as to move the first end of the optical-filter cartridge generally rearwardly along an arcuate path, to a position that is rearward of the first retainer; then, moving the cartridge generally toward the first end of the holder, but at an off-angle relative thereto, which off-angle is established by the rotating of the cartridge and which off-angle provides that the first retainer does not interfere with the moving of the cartridge generally toward the first end of the holder, wherein the moving of the cartridge generally toward the first end of the holder causes the cartridge to be removed from the holder.

Embodiment 24

The method of embodiment 23 wherein the second, deflectable retainer comprises a deflectable beam with a deflectable portion and wherein the deflecting of the second, deflectable retainer into the second, non-retaining position comprises manually deflecting the deflectable portion of the deflectable beam generally rearward; and, wherein after the slidable moving of the cartridge generally toward the second end of the holder and during the rotating of the cartridge, a portion of the cartridge is located between at least a portion of the second, deflectable retainer and a second-end portion of a frame of the protective headgear.

Embodiment 25

A method of removably mounting an optical-filter cartridge into a holder of a protective headgear that comprises a window laterally surrounded by a frame, the method comprising: deflecting a second, deflectable retainer that is at a second end of the holder into a second, non-retaining position in which the second, deflectable retainer does not prevent longitudinally outward movement of the second end of the cartridge past the second end of the holder; moving the cartridge toward the second end of the holder to a position in which the second end of the cartridge is longitudinally past the second, deflectable retainer and in which a portion of the cartridge is located between a deflectable portion of the second, deflectable retainer and a second-end section of the frame of the protective headgear; then rotating the cartridge about a rotation axis that is proximate the second end of the cartridge so as to move a first end of the cartridge generally forwardly along an arcuate path generally toward the frame of the protective headgear; then slidably moving the optical-filter cartridge generally longitudinally toward the first end of the holder, so as to move the first end of the cartridge into a space at least partially defined between a rearward member of the first retainer and a first-end section of the frame of the protective headgear, so that a longitudinal sidewall of the first retainer prevents any further longitudinal movement of the cartridge toward the first end of the holder; then deflecting the second, deflectable retainer into a first position in which the second, deflectable retainer prevents any longitudinally outward movement of the second end of the cartridge.

Embodiment 26

The method of embodiment 25 wherein in the absence of any externally-applied deflecting force, the second, deflectable retainer is biased toward the first, retaining position, and wherein the deflecting of the second, deflectable retainer from the first, retaining position to the second, non-retaining position is performed manually by the fingers of a person, without the use of any motorized apparatus and without the use of any tool.

Embodiment 27

The method of any of embodiments 23-26 using the protective headgear of any of embodiments 1-22.

The present application is a divisional of Ser. No. 13/761,433, filed 7 Feb. 2013, the entirety of which disclosure is incorporated by reference herein.

It will be apparent to those skilled in the art that the specific exemplary structures, features, details, configurations, etc., that are disclosed herein can be modified and/or combined in numerous embodiments. All such variations and combinations are contemplated by the inventor as being within the bounds of the conceived invention not merely those representative designs that were chosen to serve as exemplary illustrations. Thus, the scope of the present invention should not be limited to the specific illustrative structures described herein, but rather extends at least to the structures described by the language of the claims, and the equivalents of those structures. To the extent that there is a conflict or discrepancy between this specification as written and the disclosure in any document incorporated by reference herein, this specification as written will control.

What is claimed is:

1. A method of removing an optical-filter cartridge from a holder of a protective headgear that comprises a window laterally surrounded by a rear-facing frame, the optical-filter cartridge having first and second ends and the holder having first and second ends and the method comprising:

rearwardly deflecting a deflectable retainer that is at the second end of the holder and to which the second end of the optical-filter cartridge is proximate, from a first, retaining position into a second, non-retaining position in which the deflectable retainer allows laterally outward movement of the second end of the cartridge; then, slidably moving the cartridge toward the second end of the holder to move the second end of the cartridge laterally outward past the deflectable retainer and to move the first end of the cartridge laterally inward out of a space between a rearward member of a non-deflectable retainer at a first end of the holder and a first-end section of the rear-facing frame; then, rotating the cartridge to move the first end of the cartridge rearwardly along an arcuate path, to a position that is rearward of the non-deflectable retainer; then, moving the cartridge toward the first end of the holder, wherein the moving of the cartridge toward the first end of the holder causes the cartridge to be removed from the holder.

2. The method of claim 1 wherein after the slidable moving of the cartridge toward the second end of the holder, and during the rotating of the cartridge, a portion of the cartridge is located between at least a portion of the deflectable retainer and a second-end portion of the rear-facing frame of the protective headgear.

3. The method of claim 1 wherein the cartridge is rotated through an angle that is between 5 and 30 degrees.

4. The method of claim 1 wherein the cartridge is rotated through an angle that is between 9 and 15 degrees.

5. The method of claim 1 wherein the non-deflectable retainer comprises a sidewall with a forward base that is proximate a surface of the first-end section of the rear-facing frame, which sidewall comprises a protruding portion that protrudes rearwardly from the forward base of the sidewall.

6. The method of claim 1 wherein the optical-filter cartridge comprises an automatic darkening filter.

7. The method of claim 1 wherein the deflectable retainer comprises a deflectable beam with a deflectable portion that is forwardly and rearwardly deflectable between a first, forward position that is a retaining position in which a retaining tab that protrudes forwardly from the deflectable beam is positioned to prevent any laterally outward movement of the second end of the optical-filter cartridge past the deflectable beam; and, a second, rearward position that is a non-retaining position in which the retaining tab does not interfere with laterally outward movement of the second end of the optical-filter cartridge.

8. The method of claim 1 wherein the deflectable retainer integrally connected to, and molded with, a main body of the protective headgear.

9. A method of removably mounting an optical-filter cartridge into a holder of a protective headgear that comprises a window laterally surrounded by a rear-facing frame, the optical-filter cartridge having first and second ends and the holder having first and second ends and the method comprising:

rearwardly deflecting a deflectable retainer that is at a second end of the holder into a second, non-retaining position in which the deflectable retainer allows laterally outward movement of a second end of the cartridge past the second end of the holder;

moving the cartridge toward the second end of the holder to a position in which the second end of the cartridge is laterally past the deflectable retainer and in which a portion of the cartridge is located between a deflectable portion of the deflectable retainer and a second-end section of the frame of the protective headgear; then rotating the cartridge to move a first end of the cartridge forwardly along an arcuate path toward the frame of the protective headgear; then slidably moving the optical-filter cartridge toward the first end of the holder to move the first end of the cartridge into a space defined between a rearward member of a non-deflectable retainer and a first-end section of the frame of the protective headgear, so that a sidewall of the non-deflectable retainer prevents any further movement of the cartridge toward the first end of the holder; then deflecting the deflectable retainer into a first, retaining position in which the deflectable retainer prevents any laterally outward movement of the second end of the cartridge.

10. The method of claim 9 wherein in the absence of any externally-applied deflecting force applied manually by the fingers of a user, the deflectable retainer is biased toward the first, retaining position, and wherein the deflecting of the-deflectable retainer from the first, retaining position to the second, non-retaining position is performed manually by the fingers of a user, without the use of any motorized apparatus and without the use of any tool.

11. The method of claim 9 wherein the optical-filter cartridge is not an automatic darkening filter.

12. The method of claim 9 wherein the deflectable retainer comprises a deflectable beam with a deflectable portion that is forwardly and rearwardly deflectable between a first, forward position that is a retaining position in which a retaining tab that protrudes forwardly from the deflectable beam is positioned to prevent any laterally outward movement of the second end of the optical-filter cartridge past the deflectable beam; and, a second, rearward position that is a non-retaining position in which the retaining tab does not interfere with laterally outward movement of the second end of the optical-filter cartridge.

13. The method of claim 12 wherein the deflectable beam of the deflectable retainer is made of the same material as other components of the deflectable retainer, and, wherein the deflectable retainer is integrally connected to, and molded with, a main body of the protective headgear.

* * * * *

UNITED STATES PATENT AND TRADEMARK OFFICE
CERTIFICATE OF CORRECTION

PATENT NO. : 9,861,530 B2
APPLICATION NO. : 14/925620
DATED : January 9, 2018
INVENTOR(S) : Niklas Lilenthal Page 1 of 1

It is certified that error appears in the above-identified patent and that said Letters Patent is hereby corrected as shown below:

In the Claims

Column 22
Line 49, In Claim 8, before "integrally" insert -- is --.

Signed and Sealed this
Eleventh Day of June, 2019

Andrei Iancu
*Director of the United States Patent and Trademark Office*